United States Patent [19]
Lewis et al.

[11] Patent Number: 5,792,960
[45] Date of Patent: Aug. 11, 1998

[54] TOOL FOR MEASURING DECAY IN WOOD

[75] Inventors: David Anthony Lewis; Geoffrey Neville Boughton, both of Bentley, Australia

[73] Assignees: The Electricity Corporation, Perth; Curtin University of Technology, Bentley, both of Australia

[21] Appl. No.: 653,656

[22] Filed: May 24, 1996

[30] Foreign Application Priority Data

May 26, 1995 [AU] Australia ................... PN3215

[51] Int. Cl.$^6$ ................................................ G01M 5/00
[52] U.S. Cl. ........................... 73/786; 73/81; 73/85
[58] Field of Search ........................ 73/786, 849, 81, 73/85, 579, 12.09

[56] References Cited

U.S. PATENT DOCUMENTS

| | | | |
|---|---|---|---|
| 2,854,847 | 10/1958 | Brady | 73/849 X |
| 3,600,937 | 8/1971 | Nilberg | 73/598 X |
| 3,793,881 | 2/1974 | Hallock, Jr. | 73/841 X |
| 3,877,294 | 4/1975 | Shaw | 73/67.2 |
| 4,059,988 | 11/1977 | Shaw | 73/579 |
| 4,249,414 | 2/1981 | Barth | 73/85 X |
| 4,329,882 | 5/1982 | Kaup . | |
| 4,343,179 | 8/1982 | Astrom et al. | 73/81 |
| 4,350,044 | 9/1982 | Richardson et al. | 73/632 X |
| 4,640,119 | 2/1987 | Ludwig | 73/12.09 |
| 4,671,105 | 6/1987 | Kamm et al. | 73/85 X |
| 4,702,111 | 10/1987 | Holland | 73/579 |
| 4,748,855 | 6/1988 | Barnoff . | |
| 4,926,691 | 5/1990 | Franklin et al. | 73/579 |
| 5,051,919 | 9/1991 | Deuar | 73/786 X |
| 5,212,654 | 5/1993 | Deuar | 73/786 X |
| 5,567,871 | 10/1996 | Sandoz | 73/85 |

FOREIGN PATENT DOCUMENTS

| | | |
|---|---|---|
| 66939/86 A | 6/1987 | Australia . |
| 841959 | 2/1953 | Germany . |
| 4411746 | 10/1995 | Germany . |
| 1 284 072 | 8/1968 | United Kingdom . |
| 2 242 029 | 9/1991 | United Kingdom . |
| WO 86/01294 | 2/1986 | WIPO . |

*Primary Examiner*—Elizabeth L. Dougherty
*Attorney, Agent, or Firm*—Collard & Roe, P.C.

[57] ABSTRACT

A tool for measuring the extent of decay in a wooden object, comprising an elongated probe adapted to be inserted in an inspection hole drilled in the wooden object. The tool has at least one barb protruding therefrom adjacent to one end of the probe. The barb is designed to engage a side wall of the inspection hole so as to shear wood fibers in the side wall as the probe is withdrawn. There is indicator mechanically coupled to the probe for measuring the amount of pull-force required to shear the wood fibers in the inspection hole. The indicator includes a deflector mechanically connected to the other end of the probe and adapted to provide a measurable deflection as the pull-force required to shear the wood fibers increases. In use, when the pull-force exceeds a predetermined value, the indicator provides an indication of a transition within the wooden object from decaying wood to sound wood.

8 Claims, 3 Drawing Sheets

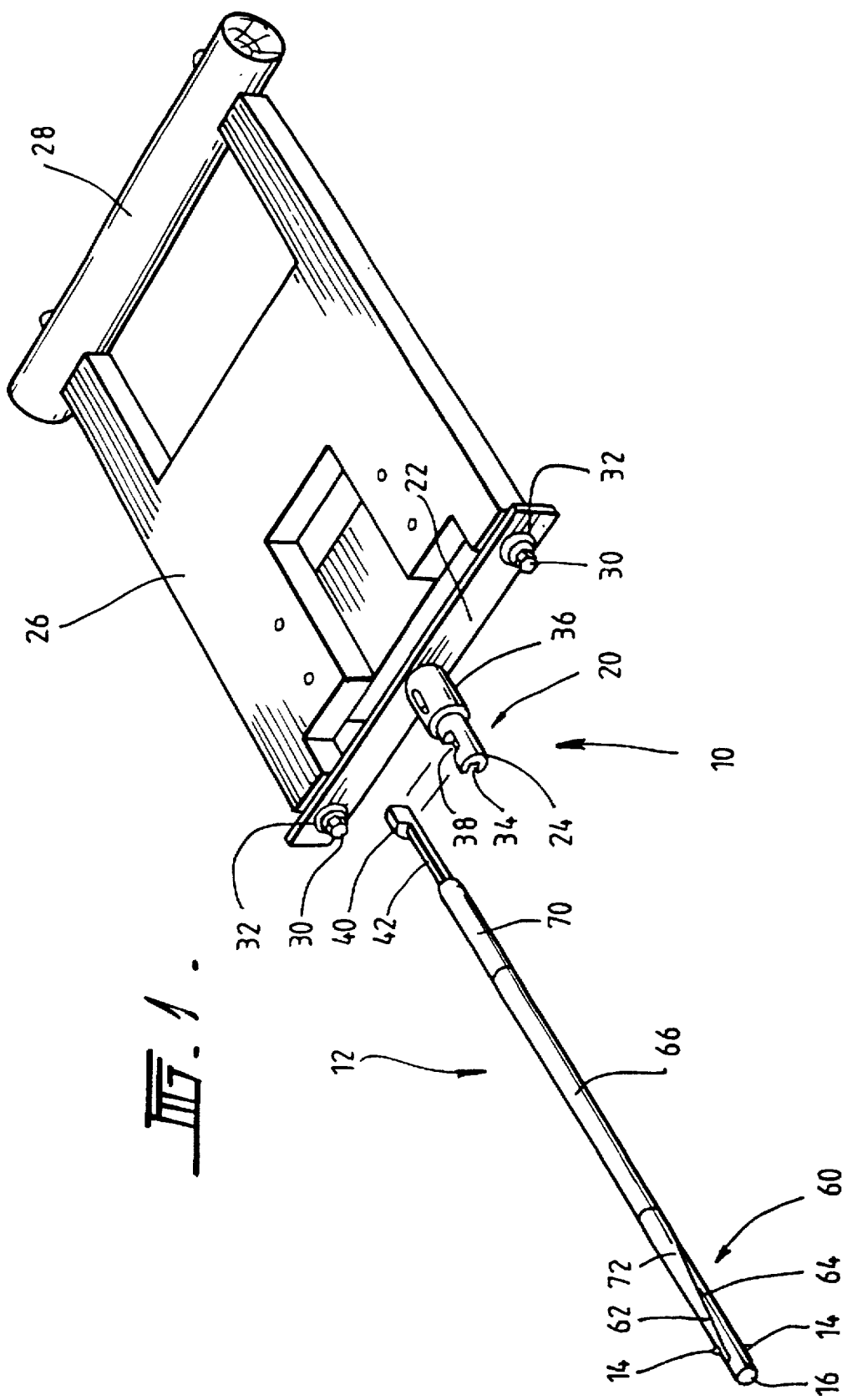

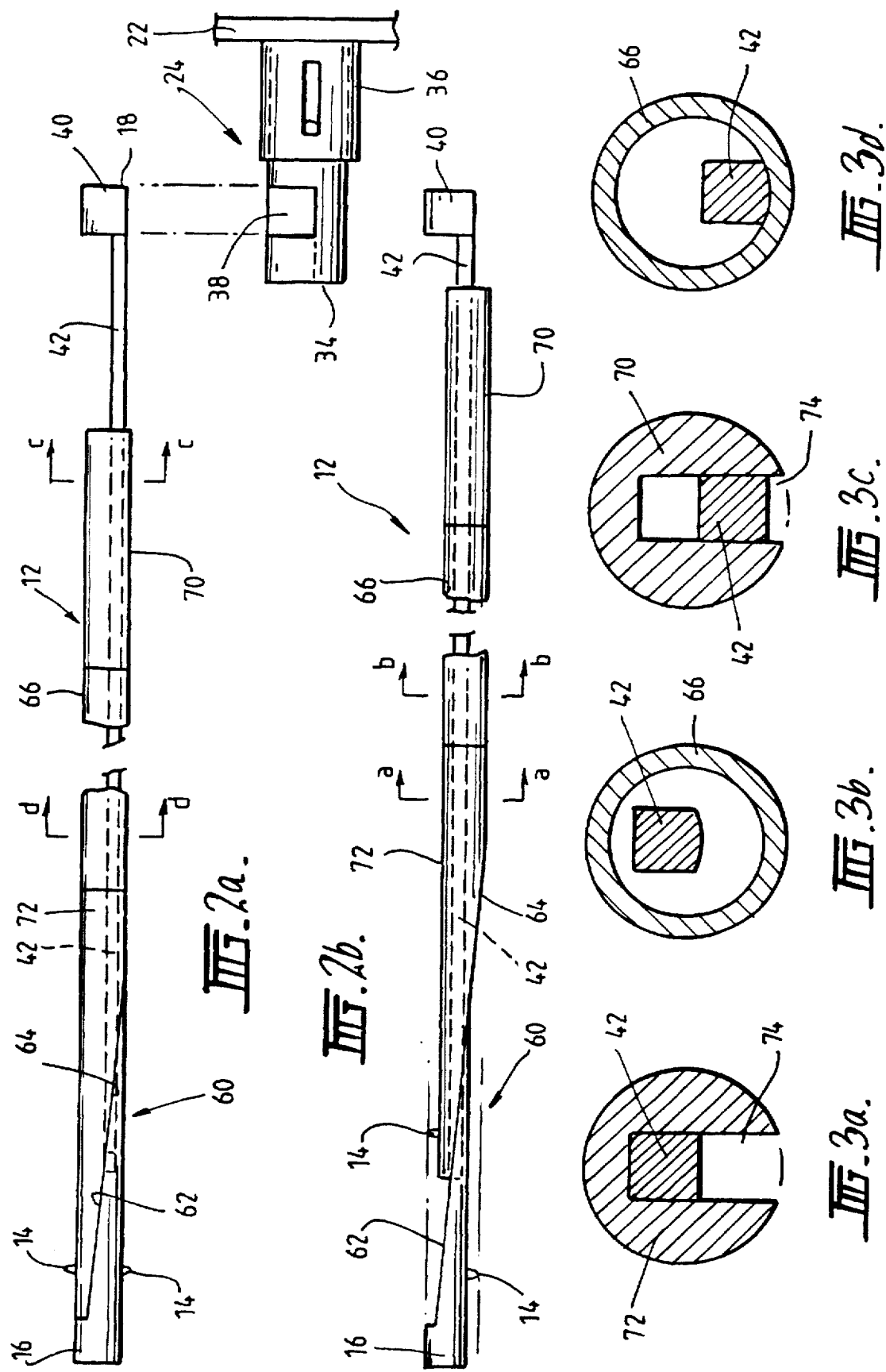

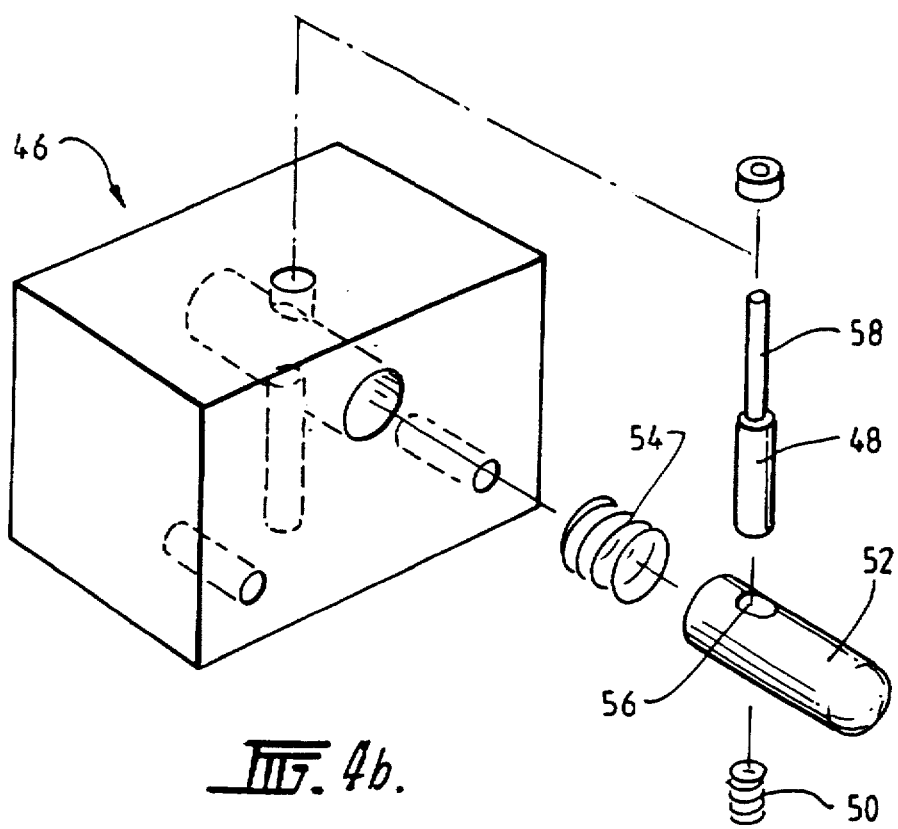
FIG. 4b.
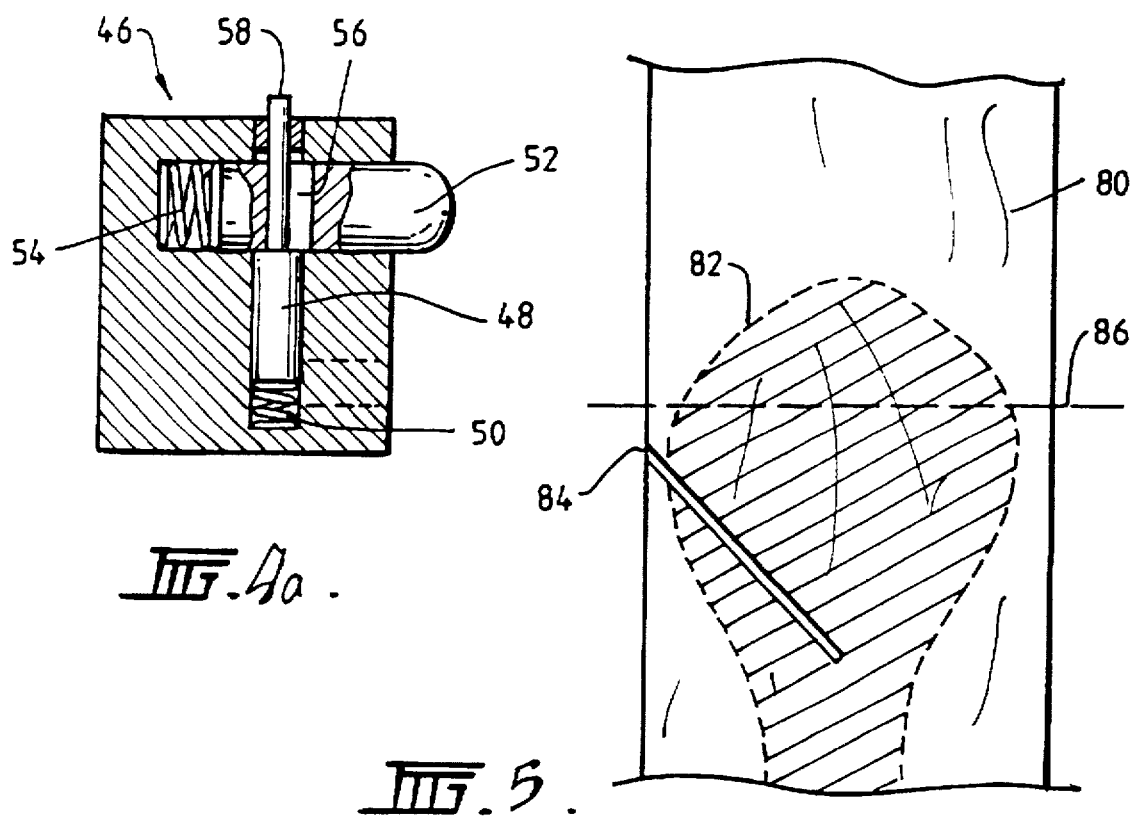
FIG. 4a.
FIG. 5.

TOOL FOR MEASURING DECAY IN WOOD

FIELD OF THE INVENTION

The present invention relates to a tool for measuring the extent of internal decay in a wooden object and relates particularly, although not exclusively, to a tool for detecting the extent of internal decay in wooden power poles.

BACKGROUND TO THE INVENTION

In the State of Western Australia alone, the Electricity Corporation (trading as Western Power) has over six hundred thousand wooden power poles in service. The majority of these wooden power poles are made from jarrah wood, which is a hard wood from a particular species of eucalypt which is native to Western Australia. Wooden power poles, including jarrah poles, are susceptible to external and internal decay which destroys the structure and reduces the density of the wood causing loss of strength and integrity. Whilst a degree of decay is tolerable, if the decay becomes too severe the pole is no longer safe to remain in service and must be either reinforced or replaced. To determine when reinforcing or replacement is necessary, Western Power employs inspection crews to periodically inspect each wooden power pole for external and internal decay. By determining the proportion of sound wood remaining in the pole, an assessment of the pole serviceability can be made.

Jarrah wood is susceptible to decay due to fungal attack. Three main types of fungal decay have been identified, namely, brown rot, white rot and soft rot. The brown rot fungi attacks the cellulose of the wood, leaving behind the darker lignin, and can result in up to 65% weight loss in the timber. The white rot fungi attacks the lignin of the wood and can result in up to 100% weight loss in the timber. The most significant difference between brown and white rot is that the extent of decay due to white rot can be seen, whereas with brown rot it is not readily apparent. Soft rot is found in the exposed superficial layer of wood and extends inwards. The decayed wood is usually of dark colouration and is soft and spongy.

The most susceptible area of a wooden power pole to decay is the area extending from 100 mm above ground level to 350 mm below ground level.

Current groundline inspection procedures for power poles involve a series of tests to assess the strength and integrity of the wood in the area most susceptible to decay. The first test is a preliminary sound test which involves striking the pole firmly with a hammer. A pole with internal decay gives a hollow or dull sound. However, this test can be misleading, even for experienced inspectors. A second test involves probing the surface of the pole with a sharp object, such as the point of a knife or screw driver, to detect the presence of any surface decay. Neither of the above tests can be used reliably for detecting the presence or extent of internal decay.

At present, the only effective procedure for testing the poles for internal decay is the boring test. This involves boring one or more holes into the pole and examining the wood shavings. Typically, the soil at the boring position is excavated to about 200 mm below the groundline and a 12 mm hole is bored at a downwards angle of 45° starting at 100 mm below the groundline. The person drilling the hole may feel a change in the resistance of the wood, and the sound of the bit cutting into the timber may also change when degraded timber is reached. When drilling, the bit is periodically withdrawn from the hole to assess the condition of the shavings from the bottom of the hole. Sound wood shavings are generally square and chunky with a hard sharp feel, whereas decayed wood shavings may be soft and spongy. Generally, decay in wood may be indicated by a change in strength, structure, colour, density, odour or softening of the wood.

One difficulty with the boring test is that some wood may have moist fibres which appear soft and spongy but may still be sound wood. Even if the presence of decayed wood is correctly identified, it is difficult to determine the extent of decay using this method as it is not possible to precisely locate where the transition from sound wood shavings to degraded wood shavings occurs. In order to reduce this uncertainty, a barbed probe is sometimes inserted into the hole and withdrawn with the barb raking a side wall of the hole. The probe encounters more resistance when the barb encounters sound wood and may therefore provide an indication of the extent of degradation of the wood within the pole. However, it is difficult to accurately determine the transition from decayed wood to sound wood as it depends on the person withdrawing the probe being able to feel the change in resistance and where it occurs.

SUMMARY OF THE INVENTION

The present invention was developed with a view to providing a tool that can be used with the boring test to provide a more precise measurement of the extent of internal decay in a wooden object. Although the following description will be given primarily with reference to the testing of wooden power poles, it is to be understood that the tool of the invention may have wider application such as, for example, in determining the extent of internal decay in wooden beams for bridges and other wooden structures. The tool may also have application in testing for the presence and/or the extent of internal decay in live trees.

According to the present invention there is provided a tool for measuring the extent of internal decay in a wooden object, the tool comprising:

an elongate probe adapted to be inserted in an inspection hole drilled in the wooden object, and having at least one barb protruding therefrom adjacent to one end of the probe, said at least one barb being designed to engage a side wall of the inspection hole so as to shear wood fibres in the side wall as the probe is withdrawn; and, indicating means mechanically coupled to the probe for measuring the amount of pull-force required to shear the wood fibres in the inspection hole whereby, in use, when the pull-force exceeds a predetermined value said indicating means provides an indication of a transition within the wooden object from decaying wood to sound wood.

Preferably said indicating means includes a deflecting means mechanically connected to the other end of said probe and adapted to provide a measurable deflection as the pull-force required to shear the wood fibres increases. Preferably said indicating means also includes a detecting means for detecting the extent of deflection of said deflecting means and providing said indication of the transition within the wooden object when the pull-force exceeds said predetermined value.

Typically said elongate probe has two barbs protruding from diametrically opposite sides of the probe. Advantageously, said barbs are retractable barbs and said probe can be switched between first and second conditions, wherein the first condition both barbs are extended so as to engage the side wall of the inspection hole and in the second condition the barbs are retracted so as to facilitate easy insertion of the probe into the inspection hole.

In one embodiment said probe comprises a shaft of circular cross-section having a slide mechanism provided adjacent to said one end of the probe, said slide mechanism comprising first and second planar surfaces adapted to slide over one another in the region of said barbs whereby, in use, in said second condition of the probe the first and second planar surfaces are misaligned so as to reduce the overall diameter of the probe in the region of said barbs.

BRIEF DESCRIPTION OF THE DRAWINGS

In order to facilitate a more thorough understanding of the nature of the invention a prototype tool will now be described in detail, by way of example only, with reference to the accompanying drawings, in which:

FIG. 1 is a perspective view of the prototype tool;

FIGS. 2(a) and 2(b) illustrate a probe for the tool in FIG. 1 showing the barbs in the extended and retracted positions respectively;

FIGS. 3(a), 3(b), 3(c) and 3(d) are section views through the probe of FIG. 2(a);

FIGS. 4(a) and 4(b) illustrate one form of detecting means that can be used with the tool of FIG. 1; and, FIG. 5 illustrates schematically the profile of internal rot at an advanced stage in a power pole.

DETAILED DESCRIPTION OF PREFERRED EMBODIMENTS

The prototype inspection tool 10 illustrated in FIG. 1 comprises an elongate probe 12 adapted to be inserted in an inspection hole drilled in a wooden object such as a power pole. The probe 12 is provided with a pair of barbs 14 protruding therefrom adjacent to one end 16 of the probe. The barbs 14 are designed to engage a side wall of the inspection hole so as to shear the wood fibres in the side wall as the probe is withdrawn. Wood fibres are normally quite strong and resilient, however fibres in decaying wood lose their flexibility and are easily broken. The present invention uses this loss of strength of decayed wood fibres as an indicator of fungal decay or other degradation of the wood. Hence, as the probe 12 is withdrawn with the barbs 14 engaging the side wall of the inspection hole, less pull-force will be required to shear the wood fibres in the side wall if the wood adjacent the end 16 of the probe is decaying, than will be required if the wood adjacent the end 16 is sound wood. The extent of decay will vary depending of whether the fungal attack is at an early or an advanced stage. Hence, there will normally be a transition in the strength of the wood fibres between the region of decaying wood and the region of sound wood.

The inspection tool 10 is also provided with an indicating means 20 mechanically coupled to the probe 12 for measuring the amount of pull force required to shear the wood fibres in the inspection hole. When the pull force exceeds a predetermined value the indicating means 20 typically provides an indication of the transition within the wooden object from decaying wood to sound wood. The indicating means 20 may take several different forms, as will be described below in more detail.

In the prototype tool 10 the indicating means 20 includes a deflecting means in the form of a deflecting bar 22 made from heat treated spring steel. The deflecting bar 22 is mechanically connected to the other end 18 of the probe 12 by means of a locking mechanism 24 and is adapted to provide a measurable deflection as the pull-force required to shear the wood fibres increases during withdrawal of the probe 12 from the inspection hole. In the prototype, the deflecting bar 22 is mounted on an aluminium frame 26 having a wooden handle 28 provided at one end to allow the tool to be firmly grasped in use by the operator. The deflecting bar 22 is mounted on the aluminium frame 26 by means of two 6 mm diameter bolts 30 which pass through respective slots provided at each end of the deflecting bar 22, each bolt 30 being provided with a pair of 16 mm diameter turned washers 32 having a spherical top that engages with the deflecting bar 22 in the region of the slots. The provision of the slots and rounded washers 32 enable the deflecting bar 22 to deflect freely when a bending moment is applied under load.

The probe 12 of the prototype is over 300 mm in length and the aluminium frame 26 with handle 28 at one end and the deflecting bar 22 with locking mechanism 24 at the other end is of similar length. Advantageously, the probe 12 of this embodiment is designed to be removably connected to the deflecting bar 22 by means of locking mechanism 24. Not only does this make the tool 10 easier to carry when not in use, but it has the added advantage that should the probe 12 become damaged it can be easily repaired or replaced by disconnecting it from the deflecting bar 22.

The locking mechanism 24 is designed for easy and rapid connection/disconnection of the probe 12. It comprises a brass shank 34 mounted to a centre point of the deflecting bar 22 and having a brass sleeve 36 slidably mounted thereon. The shank 34 is provided with a cavity 38 designed to receive snugly therein a knob 40 of matching shape provided on the end 18 of the probe 12 (see FIG. 2(a)). When knob 40 is received in recess 38 the sleeve 36 may be slid forwards over the shank 34 so as to lock the knob 40 within the cavity 38. A key steel bar 42 connects the probe 12 to the knob 40, and is received in a slot provided in the shank 34 extending to the cavity 38.

Typically, the indicating means 20 of the inspection tool will also include a detecting means for detecting the extent of deflection of the deflecting bar 22 and thus providing an indication of the transition from decaying wood to sound wood within the wooden object when the pull-force exceeds the predetermined value. The detecting means may take the form of, for example, a simple dial gauge (not illustrated) having an actuator that abuts the deflecting bar 22 and which deflects the needle of the dial gauge when displaced by the deflection of the bar 22 under load. The dial gauge may be calibrated to provide a direct reading of the pull-force being applied to the probe 12 as measured by the deflection of the deflecting bar 22. A disadvantage of using a dial gauge as the detecting means is that the operator must keep an eye on the dial gauge whilst withdrawing the probe 12 from the inspection hole so that when the pull-force exceeds a predetermined value the transition point can be correctly identified. This may be difficult, particularly if the inspection hole is provided at an awkward position and angle. FIG. 4 illustrates an alternative form of detecting means of simple mechanical construction, which detects the extent of deflection of the deflecting bar 22 and provides an indication of the transition point.

FIG. 4 illustrates a pin firing mechanism 46 which includes a pin 48 slidably received in a hole provided in the mechanism and biased by a spring 50. An actuating finger 52 is also slidably mounted in a second hole provided in the mechanism perpendicular to the first hole receiving the pin 48. Finger 52 is also biased by a second spring 54, and is provided with a hole 56 therein (see FIG. 4(b)), of similar diameter to the hole in which the pin 48 is slidably received.

In use, the pin firing mechanism 46 is mounted on the frame 26 of the inspection tool adjacent the deflecting bar 22, with the actuating finger 52 abutting a surface of an actuating member (not illustrated) clamped to the deflecting bar 22 so that deflection of the deflecting bar 22 is transferred to the actuating finger 52 of the pin firing mechanism 46. Hence, when deflecting bar 22 bows outwards under load, actuating finger 52 will be pushed inwards against the force of spring 54 by the same distance.

In FIG. 4(a) it can be clearly seen that when the hole 56 in actuating finger 52 is misaligned with the pin 48 in the firing mechanism, the pin 48 is prevented from popping up. However, once the finger 52 is pushed inwards due to the deflection of the deflecting bar 22, hole 56 will become aligned with the pin 48 at a predetermined deflection and the protruding end 58 of pin 48 will pop up to indicate that the predetermined deflection has been reached. This predetermined deflection can be set so as to correspond to a predetermined load on the deflecting bar 22, which in turn provides an indication of the pull-force required to withdraw the probe 12 from the inspection hole.

Calibration of the prototype tool 10 using 12 mm inspection holes drilled into power poles made from jarrah wood, established that an average deflection of 1.7 mm indicated the transition of decayed wood to sound wood, corresponding to a pull-force of 174N. It is a relatively simple matter to mount the firing mechanism 46 on the frame 26 of the tool in such a way that the actuating finger 52 need only be displaced by 1.7 mm in order to "fire" the pin 48, and thus indicate that the transition has been reached. Clearly, the inspection tool 10 can be calibrated for other types of wood, which may require a smaller or a larger deflection, corresponding to a smaller or larger pull-force, in order to provide an indication of the transition from decaying to sound wood within the wooden object.

An important feature of the inspection tool is the provision of at least one barb 14 on the probe 12 for shearing the wood fibres in the side wall of the inspection hole as the probe is withdrawn. The probe 12 of the prototype tool 10 is in the form of a shaft of circular cross-section and is provided with two barbs 14 on diametrically opposite sides of the shaft adjacent to end 16 of the probe. The provision of two barbs on opposite sides of the probe ensures that wood fibres on both sides of the inspection hole are being sheared by the barbs, and therefore reduces the possibility of not detecting a decayed region of wood within the hole. Also, the provision of two barbs 14 means that an increased pull-force is required to withdraw the probe when the barbs 14 encounter sound wood, thereby making the transition from decaying wood to sound more pronounced. However, in order to be able to insert the probe 12 into the hole without damaging the hole walls or the probe, it is desirable that the barbs 14 can be retracted from their protruding position. The ability to retract the barbs 14 is also desirable in a situation where the probe becomes lodged in the inspection hole, so that the barbs can be withdrawn from engagement with the walls of the hole and the probe easily recovered.

In order to facilitate both retraction and extension of the barbs 14, a slide mechanism 60 is provided adjacent the end 16 of the probe in the region of the barbs 14. As can be seen most clearly in FIG. 2, the slide mechanism 60 comprises first and second planar surfaces 62, 64 adapted to slide over one another in the region of the barbs 14. FIG. 2(a) illustrates the probe 12 in a testing mode wherein both barbs 14 are extended so as to engage the side wall of the inspection hole, whereas FIG. 2(b) illustrates the probe in an insertion mode in which the barbs 14 are retracted so as to facilitate easy insertion of the probe into the inspection hole. In the insertion mode of the probe as shown in FIG. 2(b) the second planar surface 64 has been slid back over the first planar surface 62 away from the end 16 of the probe. Because the first and second planar surfaces 62, 64 are inclined with respect to the longitudinal axis of the probe 12, this misalignment of the planar surfaces 62, 64 has the effect of reducing the overall diameter of the shaft of the probe in the region of the barbs 14. In the testing mode of the probe as illustrated in FIG. 2(a) the overall diameter of the probe in the region of the barbs 14 is approximately 15 mm from point to point of the barbs 14, whereas the overall diameter of the probe in the region of the barbs in the second condition as illustrated in FIG. 2(b) is approximately 12 mm, which corresponds to the preferred diameter of an inspection hole in which the probe is inserted. Barbs 14 are typically manufactured from hardened steel and are screwed into threaded holes provided in the shaft of the probe adjacent the end 16. The barbs 14 of this embodiment protrude approximately 1.5 mm from the outer circumferential surface of the probe shaft.

The probe shaft of the prototype tool 10 has an outer diameter of approximately 9 mm, and therefore when drilling an inspection hole in the power pole it is important that a 12 mm drill bit be used so that when the barbs 14 protrude in the extended position they will engage a side wall of the inspection hole. Clearly, the shaft of the probe 12 can be made of any suitable diameter, provided the inspection hole is of a matching size. The outer surface of the probe shaft is provided with a series of markings (not visible) at equal spaced intervals along the length of the probe shaft, to provide an indication of the extent to which the probe has been inserted and subsequently withdrawn from the inspection hole during testing. When the transition point is reached, a visual inspection of these markings will provide a measure of the distance from the barbs 14 (where the transition is located) to the mouth of the inspection hole 84.

In order to facilitate the sliding movement of the slide mechanism 60, the shaft of the probe 12 is provided with a moveable portion 66 the bulk of which is formed by a hollow brass tube having an outer diameter of 9 mm fitted with first and second lengths of brass rod 70, 72 at both ends (see FIG. 2). The lengths of brass rod also have an outer diameter of 9 mm and are both provided with a channel 74 cut longitudinally therethrough and sized to accommodate the key steel bar 42 therein. Key steel bar 42 passes all the way through the moveable portion 66 of the probe shaft and is connected to the end 16 of the probe shaft, which is also formed from a length of solid brass rod having an outside diameter of 9 mm.

FIGS. 3(a) and (c) illustrate a section view through the lines A—A and C—C in FIG. 2(a). In both drawings the location of the key steel bar 42 within the channel 74 is clearly visible. FIG. 3(a) illustrates the position of the key steel bar 42 when the probe 12 is in the insertion mode, namely, when the barbs 14 are retracted. FIG. 3(c) illustrates the position of the key steel bar 42 within the channel 74 when the probe 12 is in the testing mode, namely, with the barbs 14 extended. It will be seen that when the first and second planar surfaces 62, 64 of the slide mechanism 60 are moved with respect to each other, the key steel bar 42 can move up or down within the channel 74 in order to accommodate the reduction in overall diameter of the probe in the region of the barbs 14. FIGS. 3(b) and (d) both illustrate a section view through the hollow tube 68 at the line B—B in FIG. 2(a). Once again, the changing position of the key steel bar 42 in the two operating modes of the tool is clearly illustrated. In use, the probe 12 can quickly be switched from the testing mode to the insertion mode, or vice versa, by the operator simply gripping the outer surface of the moveable portion 66 of the probe and sliding it backwards or forwards along the key steel bar 42 so that the first and second planar surfaces 62, 64 slide over one another to move the barbs 14 to the extended or the retracted position as required.

A preferred method of using the inspection tool 10 will now be briefly described with particular reference to FIG. 5. FIG. 5 is a section view through a wooden power pole 80 showing the profile of an internal rot pattern 82 due to fungal attack which is at an advanced stage. A preferred testing method using the inspection tool 10 involves drilling an inspection hole 84 at 45° to the longitudinal axis of the pole from approximately 100 mm below groundline 86. Through extensive testing, it has been found that drilling an inspection hole at this level and angle will most frequently intercept the area of worst internal rot of the pole. The probe 12 is fitted to the deflecting bar 22 of the inspection tool by means of the locking mechanism 24, and then the probe is switched to the insertion mode, in which the barbs 14 are retracted, by sliding the moveable portion 66 of the barb backwards as shown in FIG. 2(b). The end 16 of the probe is then inserted into the inspection hole 84 and pushed downwards until the end 16 of the probe reaches approximately the centre of the power pole 80. Then the probe 12 is switched to the testing mode by pushing downwards on the first length of rod 70 so as to cause the second planar surface 64 on the moveable portion 66 to slide over the first planar surface 62 until the planar surfaces are realigned with the barbs 14 in the extended positions as shown in FIG. 2(a). A small notch is provided adjacent the end 16 of the probe which, together with the constraining effect of the walls of the inspection hole 84, prevents the second planar surface 64 from over-shooting the first planar surface 62 when switching to the testing mode.

Once the probe 12 has been switched to the testing mode, it is then withdrawn from the inspection hole 84 by pulling on the handle 28 of the inspection tool 10. As the probe is withdrawn from the inspection hole, the resistance offered to the barbs 14 by the wood fibres in the region of decaying wood remains relatively constant. However, when the barbs 14 cross the transition to sound wood, the pull-force required to continue to withdraw the probe 12 from the inspection hole increases substantially. As noted above, in jarrah power poles using a 12 mm inspection hole, a pull-force of approximately 174N was found to be the most effective indicator of the transition from decayed to sound wood. The pin firing mechanism 46 of the prototype is calibrated to "fire" the pin 58 when this predetermined pull-force is reached, so as to provide a visual and audible indication to the operator that the transition from decaying wood to sound wood has been reached.

In practice, it was found occasionally during testing that the probe 12 became lodged within the inspection hole until the pull-force was increased substantially which resulted in the probe "jumping" a distance before the barbs 14 became embedded again. During this "jump" the pin was fired but it was difficult to determine at what depth this occurred. This difficulty may be readily overcome by stipulating that the tool must be stationary when the pin fires. This means that if the probe "jumps" the pin should be reset and the test continued until a point is reached where a static pull-force produces a "click" of the firing pin 48. If the operator is unsure about the portion of the inspection hole that the tool "jumped", he can simply reinsert the tool to test that portion again simply by switching the probe from the testing mode to the insertion mode. The same inspection hole may be tested several times in this way until a consistent reading for the transition point is reached. Two or more holes may be drilled into the power pole at different angles and heights relative to the groundline in order to obtain further readings for the presence and extent of internal decay within the power pole.

From the above detailed description of a prototype inspection tool in accordance with the invention, it will be appreciated that the tool provides a more reliable means of testing for the presence and extent of internal decay in wooden objects such a power poles. By eliminating some of the guess work and subjective impressions of the Inspector, the tool enables a more accurate determination of the extent of internal decay to be made. The tool is also simple to operate and of relatively inexpensive construction.

Numerous variations and modifications will suggest themselves to persons skilled in the relevant arts, in addition to those already described, without departing from the basic inventive concepts. For example, the indicating means of the prototype tool for measuring the amount of pull-force required to shear the wood fibres in the inspection hole is of relatively simple mechanical construction. However, more sophisticated indicating means may be employed to measure the amount of pull-force and to provide an indication of the transition within the wooden object from decaying wood to sound wood. For example, one or more strain gauges may be coupled to the probe and connected to electronic processing means which calculates the pull-force, and may be provided with a visual display and/or audible output to indicate when the pull-force exceeds the predetermined value. One advantage of such an electronic indicating means is that it would enable the tool to be more quickly calibrated for different types of wood. Also the tool could be set to determine the location of sound wood by evaluating the variation in the pull force within the pole rather than using a predetermined absolute value. The probe of the tool may also be fitted with means for automatically measuring the distance that the probe has been inserted into the inspection hole and subsequently withdrawn when the transition point is reached. All such variations and modifications are to be considered within the scope of the present invention, the nature of which is to be determined from the foregoing description.

We claim:

1. A tool for measuring the extent of internal decay in a wooden object, the tool comprising:

an elongated probe adapted to be inserted in an inspection hole drilled in the wooden object, and having at least one barb protruding therefrom adjacent to one end of the probe, said at least one barb being designed to engage a side wall of the inspection hole so as to shear wood fibers in the side wall as the probe is withdrawn; and indicating means mechanically coupled to the probe for measuring the amount of pull-force required to shear the wood fibers in the inspection hole, wherein said indicating means includes a deflecting means mechanically connected to the other end of said probe and adapted to provide a measurable deflection as the pull-force required to shear the wood fibers increases whereby, in use, when the pull-force exceeds a predetermined value said indicating means provides an indication of a transition within the wooden object from decaying wood to sound wood.

2. A tool as defined in claim 1, wherein said indicating means also includes a detecting means for detecting the extent of deflection of said deflecting means and providing said indication of the transition within the wooden object when the pull-force exceeds said predetermined value.

3. A tool as defined in claim 2, wherein said indicating means comprises a pin firing mechanism having a pin slidably received in a first hole provided in the mechanism and biased by a first spring, and an actuating finger slidably mounted in a second hole provided perpendicular to the first hole and biased by a second spring, said actuating finger having a third hole therein of similar diameter to the first and adapted to receive the pin therein when the first and third holes become aligned so that the pin can pop up to indicate a predetermined deflection of the deflecting means, said actuating finger being moved by said deflecting means in use.

4. A tool as defined in claim 1, wherein said elongate probe has two barbs protruding from diametrically opposite sides of the probe.

5. A tool as defined in claim 4, wherein said barbs are retractable barbs and said probe can be switched between first and second conditions, wherein the first condition both barbs are extended so as to engage the side wall of the inspection hole and in the second condition the barbs are retracted so as to facilitate easy insertion of the probe into the inspection hole.

6. A tool as defined in claim 5, wherein said probe comprises a shaft of circular cross-section having a slide mechanism provided adjacent to said one end of the probe, said slide mechanism comprising first and second planar surfaces adapted to slide over one another in the region of said barbs whereby, in use, in said second condition of the probe the first and second planar surfaces are misaligned so as to reduce the overall diameter of the probe in the region of said barbs.

7. A tool as defined in claim 1, wherein said probe is removably connected to the tool by a locking mechanism, whereby the probe may be disconnected from the tool for transport or replacement.

8. A tool as defined in claim 1, further comprising a support frame provided with a handle at one end for gripping the tool when inserting and retracting the probe in an inspection hole.

* * * * *